United States Patent
Hastings et al.

(10) Patent No.: US 7,706,891 B2
(45) Date of Patent: Apr. 27, 2010

(54) CATHETER EMPLOYING SHAPE MEMORY ALLOY SHAPING WIRE OR PULL WIRE AND METHOD OF ITS MANUFACTURE

(75) Inventors: John M. Hastings, Minneapolis, MN (US); Gary B. LaTraille, Maple Grove, MN (US); Richard E. Stehr, Stillwater, MN (US); Allan M. Fuentes, Mound, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 385 days.

(21) Appl. No.: 11/723,729

(22) Filed: Mar. 21, 2007

(65) Prior Publication Data

US 2008/0234661 A1 Sep. 25, 2008

(51) Int. Cl.
*A61N 1/00* (2006.01)
(52) U.S. Cl. ...................................... 607/115
(58) Field of Classification Search ................. 148/237; 439/620.1; 606/129, 200; 600/585; 607/116
See application file for complete search history.

(56) References Cited

U.S. PATENT DOCUMENTS

| | | | |
|---|---|---|---|
| 4,559,951 A | 12/1985 | Dahl et al. | |
| 5,357,979 A * | 10/1994 | Imran | 600/585 |
| 5,938,694 A | 8/1999 | Jaraczewski et al. | |
| 6,231,570 B1 | 5/2001 | Tu et al. | |
| 6,882,887 B1 | 4/2005 | Shelchuk et al. | |
| 7,052,493 B2 | 5/2006 | Vaska et al. | |
| 2006/0167536 A1 | 7/2006 | Nygren et al. | |

FOREIGN PATENT DOCUMENTS

| | | | |
|---|---|---|---|
| JP | 07178539 A | * | 7/1995 |
| JP | 2004237349 A | * | 8/2004 |

OTHER PUBLICATIONS

International Search Report for PCT/US08/54971 filed Feb. 26, 2008, and Written Opinion dated Aug. 15, 2008.

* cited by examiner

*Primary Examiner*—George Manuel
*Assistant Examiner*—Robert N Wieland
(74) *Attorney, Agent, or Firm*—Wiley Rein LLP (57) ABSTRACT

An electrophysiology catheter includes an elongate catheter body having a distal end and a proximal end, a catheter tip including at least one metallic catheter component, such as an electrode, thereon, and at least one internal catheter component joined to the at least one metallic catheter component. The at least one internal catheter component includes a shape memory alloy and a metal compound that is capable of both bonding with the shape memory alloy and being metallurgically joined to the at least one metallic catheter component as by brazing. The metal compound may be a coating on or a core within the shape memory alloy. Suitable metal compounds include, without limitation, nickel, copper, brass, and combinations thereof.

40 Claims, 6 Drawing Sheets

CATHETER EMPLOYING SHAPE MEMORY ALLOY SHAPING WIRE OR PULL WIRE AND METHOD OF ITS MANUFACTURE

BACKGROUND OF THE INVENTION a. Field of the Invention

The instant invention relates to catheters. In particular, the instant invention relates to catheters employing shape memory alloy wires as shaping wires and/or pull wires.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

To increase the ability to move and navigate a catheter within a patient's body, steerable catheters have been designed. Steerable catheters are often manipulated by selectively tensioning one or more pull wires running along the length of the catheter, typically offset from a central axis of the catheter, thereby deflecting the distal end of the steerable catheter in one or more planes. Steerable catheters may also utilize shaping wires that form the distal end of the catheter into a desired, preset geometry to facilitate proper positioning of the catheter within the patient's body. These pull wires and shaping wires are often attached to a metallic catheter component located at the distal end of the catheter, such as one of the electrodes carried on the distal end of the catheter or a pull ring incorporated in the catheter, through a metallurgical joining process such as silver brazing.

It is sometimes desirable to utilize shape memory alloys, such as nickel-titanium, in pull wires and shaping wires. Shape memory alloy pull wires are desirable in that they facilitate restoring the distal end of the catheter to an undeflected position when the pull wires are unloaded (e.g., not in tension) by tending to return to their undeformed shape. Shape memory alloy shaping wires are desirable in that they permit the catheter to rebound to a preset geometry after deformation, such as application of a straightening device in order to insert the catheter into the patient's body through a relatively small incision.

Since it is difficult to metallurgically join shape memory alloys to other metals, such as those typically employed in catheter electrodes or pull rings, it is known to provide a short stainless steel sleeve, commonly called a crimp sleeve, over the distal end of the shape memory alloy wire. The crimp sleeve is typically mechanically fastened to the distal end of the shape memory alloy wire, and the crimp sleeve is then metallurgically joined to the tip electrode or other metallic catheter component.

As catheters are used in smaller and smaller passages, there is a growing need to use catheters that have a smaller outer dimension. Accordingly, there is a need to use steerable catheters that have smaller cross-sections. The use of a crimp sleeve about the distal end of the shape memory alloy wire, however, increases the outer diameter of the shape memory alloy wire by between about 0.006" and about 0.010". This may make it more difficult to manufacture catheters of reduced outside diameter, and may also undesirably restrict the maximum outer diameter of the shape memory alloy wire than can be employed in a catheter having a particular outside diameter.

BRIEF SUMMARY OF THE INVENTION

It is therefore desirable to be able to join a shape memory alloy wire to the distal end of a catheter without substantially increasing the outer diameter of the shape memory alloy wire.

It is also desirable to provide a catheter of reduced outer diameter incorporating a shape memory alloy wire.

It is also desirable to increase the outer diameter of a shape memory alloy wire that may be employed in a catheter of a particular outside diameter, thereby improving the stiffness of the catheter.

Disclosed herein is a catheter that includes: an elongate catheter body having a proximal end and a distal end; at least one metallic catheter component located at the distal end of the elongate catheter body; and at least one shape memory alloy wire extending at least partially along the elongate catheter body and having a proximal end and a distal end, wherein at least the distal end of the at least one shape memory alloy wire is plated with a plating metal that is compatible to be metallurgically joined to the at least one metallic catheter component, and wherein the distal end of the at least one shape memory alloy wire is joined to the at least one metallic catheter component positioned on the distal end of the elongate body.

The shape memory alloy wire may include nickel-titanium, copper-aluminum-nickel, copper-zinc-aluminum, or some combination thereof. The shape memory alloy wire may be configured as a pull wire that deflects the distal end of the catheter body in at least one plane, as a shaping wire that forms the distal end of the catheter body into a preset shape, or as a combination pull wire and shaping wire.

Suitable plating metals include, without limitation, nickel, copper, brass, and combinations thereof. The plating metal preferably increases an outer dimension (e.g., outer diameter) of the at least one shape memory alloy wire by no more than about 0.0010", and more preferably by no more than about 0.0005". Preferably, the distal end of the catheter body has an outer diameter of about 5 French, with the at least one shape memory alloy wire having an outer diameter of about 0.15". However, the distal end of the catheter body may also have an outer diameter of less than about 4 French, or even of less than about 3 French.

The at least one shape memory alloy wire is typically brazed to the at least one metallic catheter component, and is preferably silver brazed thereto. For example, in some embodiments of the invention, the at least one shape memory alloy wire is metallurgically joined to a tip electrode. In other embodiments of the invention, the at least one shape memory alloy wire is metallurgically joined to a pull ring.

Also disclosed herein is an electrophysiology catheter including: a catheter body having a distal end and a proximal end; a tip electrode attached to the distal end of the catheter body; and at least one shape memory alloy wire extending through the catheter body, wherein a distal end of the at least one shape memory alloy wire is plated with a metal compound and the plated end of the at least one shape memory alloy wire is metallurgically joined to the tip electrode. The metal compound may be selected from the group consisting of nickel, copper, brass, and any combination thereof, while the shape memory alloy wire may include a material selected from the group consisting of nickel-titanium, copper-aluminum-nickel, and copper-zinc-aluminum. Typically, the plated end of the at least one shape memory alloy wire is brazed to the tip electrode.

According to another aspect of the present invention, a method of manufacturing a catheter includes the following steps: forming an elongate catheter body having a proximal end and a distal end; attaching at least one metallic catheter component to the distal end of the catheter body; coating at least a portion of at least one shape memory alloy wire with a metal compound compatible with a metallurgical joining process; and metallurgically joining the coated portion of the at least one shape memory alloy wire to the at least one metallic catheter component. The step of coating at least a portion of at least one shape memory alloy with a metal compound compatible with a metallurgical joining process may include plating at least a portion of the shape memory alloy wire with the metal compound, such as nickel, copper, brass, or a combination thereof. One suitable metallurgical joining process is brazing, and in particular silver brazing, though other metallurgical joining processes, such as soldering and welding, are also contemplated.

In yet another aspect of the invention, an electrophysiology catheter includes: an elongate catheter body having a distal end and a proximal end; a catheter tip that comprises at least one metallic catheter component, said catheter tip being positioned on the distal end of the elongate body; and at least one internal catheter component joined to the at least one metallic catheter component, wherein the at least one internal catheter component comprises a first material and a second material, the first material being a shape memory alloy and the second material being a metal compound that is capable of bonding with the first material, and wherein the second material is metallurgically joined to the at least one metallic catheter component. The second material may be coated about the first material, for example through a plating process, or may form a core within the first material.

Also disclosed is a method of manufacturing an electrophysiology catheter. The method includes the steps of: forming a catheter body having a proximal end and a distal end; attaching a tip electrode to the distal end of the catheter body; providing at least one catheter component comprising a first material and a second material, wherein the first material is a shape memory alloy and the second material is a metal compound that is capable of bonding with the first material and being metallurgically joined to the tip electrode; and metallurgically joining the at least one catheter component to the tip electrode.

An advantage of the present invention is that it permits shape memory alloy shaping wires and/or pull wires to be metallurgically joined to a metallic catheter component without the use of a mechanically-fastened crimp sleeve or other additional, intermediate catheter component. This provides additional "real estate" in the distal end of the catheter, which may be occupied by a shape memory alloy wire of increased outer diameter where it is desirable to increase the stiffness of the catheter.

Another advantage of the present invention is that, by metallurgically joining shape memory alloy shaping wires and/or pull wires to a metallic catheter component without the use of a mechanically-fastened crimp sleeve, the overall outer diameter of the catheter may be reduced for use in smaller passages and/or vessels.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a steerable or deflectable catheter suitable for use in the human vasculature for known medical procedures, such as cardiac diagnostic and therapeutic procedures including, without limitation, electrophysiological mapping and cardiac ablation. The invention will be described in connection with a mono-directional steerable electrophysiology catheter incorporating a single shape memory alloy pull wire that is metallurgically joined to the catheter tip electrode. It is contemplated, however, that the described features may be incorporated into any number of catheters or other devices, as would be appreciated by one of ordinary skill in the art.

Figure 1:
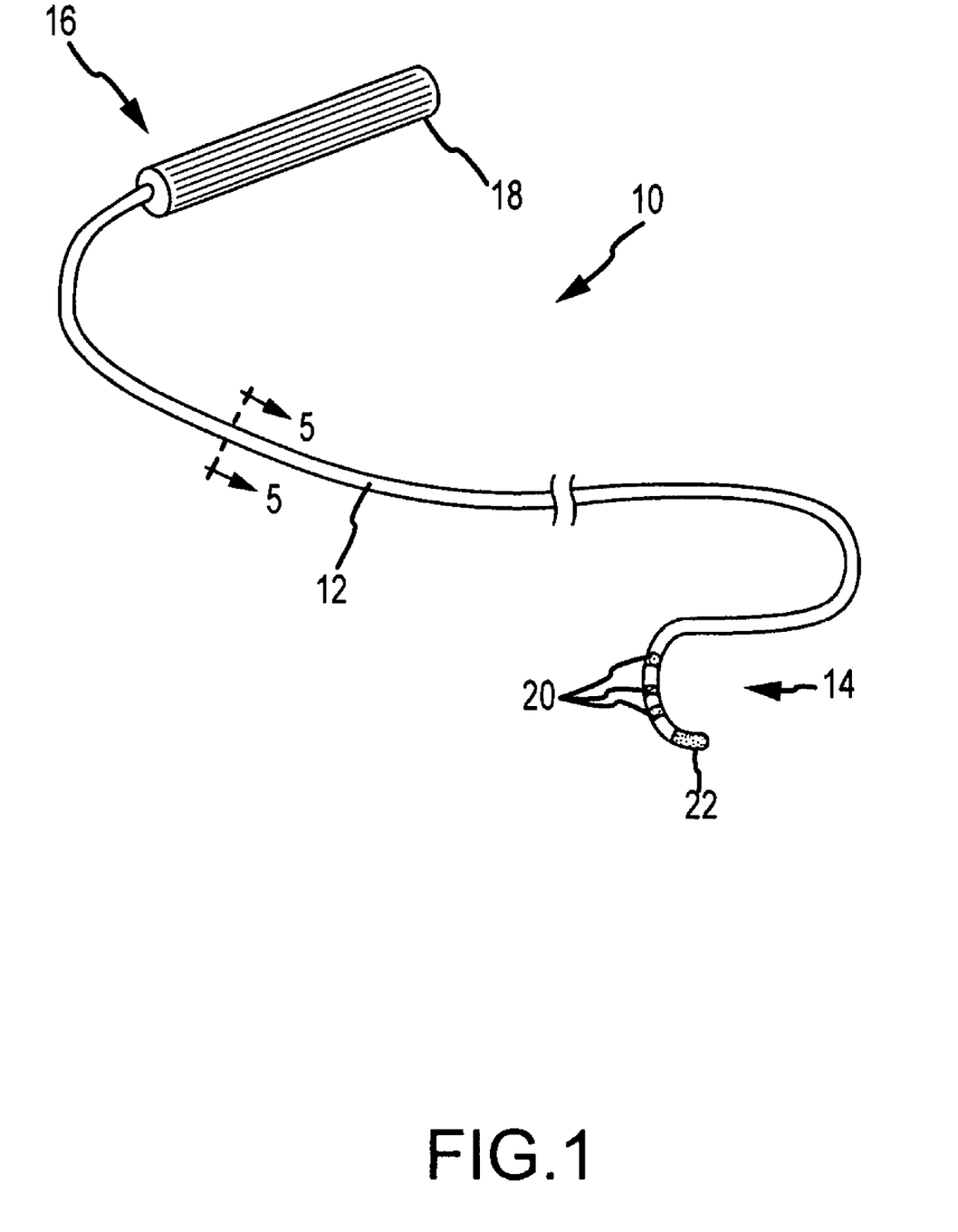
FIG. 1 is a perspective view of a catheter according to an embodiment of the present invention.

Referring now to the figures, and in particular to FIG. 1, an electrophysiology catheter 10 includes an elongate catheter body or shaft 12 having a distal end 14 and a proximal end 16. A handle 18 may be coupled to proximal end 16 of catheter body 12 to control catheter 10, for example to deflect distal end 14 of catheter body 12. A plurality of electrodes 20, including a tip electrode 22, may be located at distal end 14 of catheter body 12. By way of example only, electrodes 20, 22 may be used to deliver ablating energy to a tissue surface during an ablation procedure, for example to treat atrial fibrillation, or to measure electrophysiological characteristics during a diagnostic procedure, for example to map conduction pathways on a patient's heart. One of ordinary skill in the art will appreciate how to attach electrodes 20, 22 to catheter body 12.

One suitable method of manufacturing catheter shaft 12 will be described with reference to FIGS. 2-5. As they are assembled, the catheter components will be collectively referred to as a catheter assembly.

Figure 2:
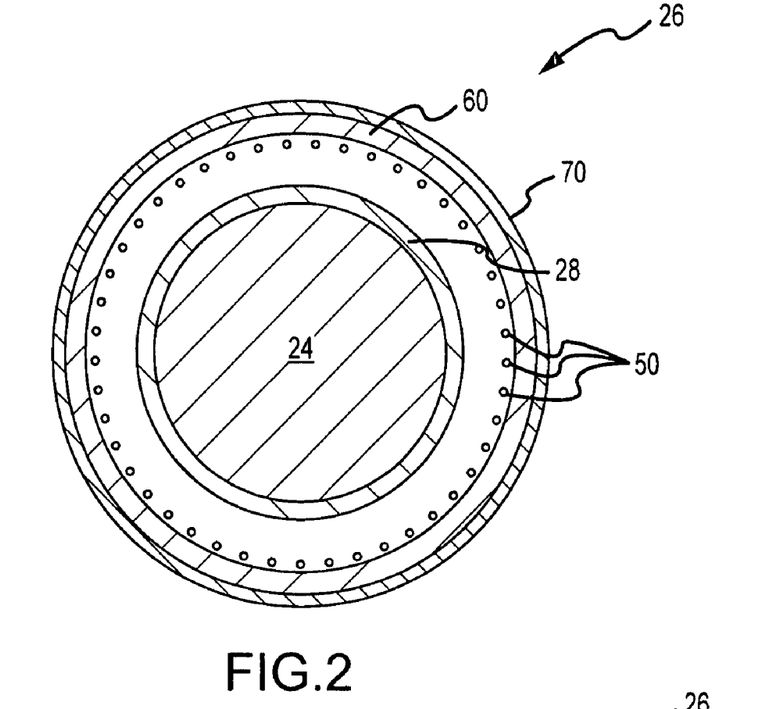
FIG. 2 is a radial cross-sectional view of a catheter body prior to the application of heat to melt process the outer layer.

FIG. 2 is a cross-sectional view of a catheter assembly prior to the application of heat to melt process the outer layer. As depicted in FIG. 2, a mandrel 24, which is preferably round in cross-section and preferably from about 6 inches to about 4 feet in length, is a component of catheter assembly 26, and may be the first component thereof during manufacture of catheter body 12. Mandrel 24 has a distal end and a proximal end. An inner liner 28 is placed on mandrel 24. Inner liner 28 may be knotted at one end (e.g., the distal end) and then fed onto mandrel 24. Of course, mandrel 24 and inner liner 28 may have any shape consistent with the desired final lumen configuration and/or intended use of catheter 10.

Preferably, inner liner 28 is an extruded polytetrafluoroethylene (PTFE) tubing, such as Teflon® brand tubing, which is available commercially. Inner liner 28 may also be made of other melt processing polymers, including, without limitation, etched polytetrafluoroethylene, polyether block amides, nylon, and other thermoplastic elastomers. Once such elastomer is Pebax®, made by Arkema, Inc. Pebax of various durometers may be used, including, without limitation, Pebax 30D to Pebax 70D. In a preferred embodiment, inner liner 28 is made of a material with a melting temperature higher than that of an outer layer 60, which will be further described below, such that inner liner 24 will withstand melt processing of outer layer 60.

Figure 4:
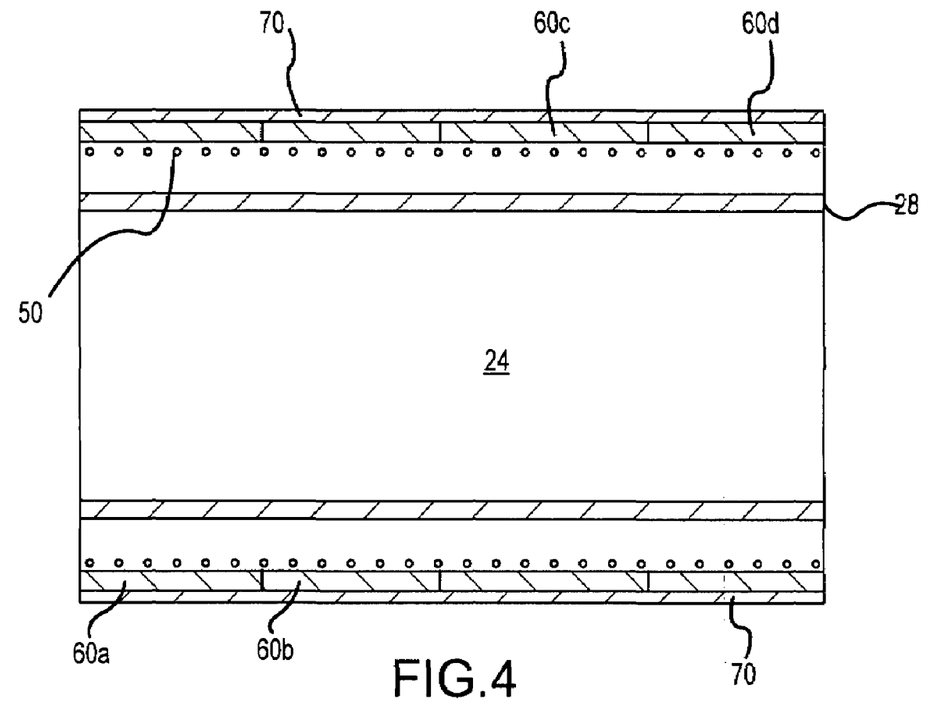
FIG. 4 is a longitudinal cross-sectional view of a catheter body prior to the application of heat to melt process the outer layer.

Outer layer 60 is then placed over inner liner 28, wire 30, and preformed tube 40 (if present). Preferably, outer layer 60 is made of one or more polymeric materials, such as any of the polymeric materials described above in connection with inner liner 28. Outer layer 60 may be made of either single or multiple sections or segments of tubing that may be either butted together or overlapped with each other, as illustrated in FIG. 4 (segments 60*a*, 60*b*, 60*c*, 60*d*), and the sections may vary in hardness and in length as desired for a particular application or intended function of catheter 10. For example, the hardness of outer layer 60 may decrease distally or proximally, or may provide a segment of increased hardness between two segments of lesser hardness. The various segments 60*a*, 60*b*, 60*c*, 60*d* will be bonded together in subsequent processing, resulting in a catheter body that has longitudinally varying stiffness, which may be desirable in certain applications of catheter 10.

It is also contemplated for outer layer 60 to include more than one concentrically-arranged layer, for example two or more layers of melt-processing polymeric material, which may vary radially in hardness. That is, a first, inner layer of outer layer 60 may have a first hardness, while a second, outer layer of outer layer 60 may have a second hardness. Preferably, if a radially-varying outer layer 60 is utilized, the second, outer layer of outer layer 60 has a lower hardness than the first, inner layer of outer layer 60.

Optionally, a braided wire assembly 50 may be placed over inner liner 28 before outer layer 60 is applied. Braided wire assembly 50 serves to both reinforce catheter body 12 and to transmit torque along the length of catheter body 12. Braided wire assembly 50 may be formed of stainless steel wire, including for example 0.003" high tensile stainless steel wire. Braided wire assembly 50 may be formed in a standard braid pattern and density, for example, about 16 wires at about 45 to about 60 picks per inch ("PPI") density. Alternatively, a braid may be used that is characterized by a varying braid density. For example, braided wire assembly 50 may be characterized by a first braid density at proximal end 16 of catheter body 12 and then transition to one or more different braid densities as braided wire assembly 50 approaches distal end 14 of catheter body 12. The braid density of distal end 14 may be greater or less than the braid density at proximal end 16. In a specific example, the braid density at the base (i.e., proximal end 16) is about 50 PPI and the braid density at distal end 14 is about 10 PPI. In another embodiment, the braid density at distal end 14 is about 20% to about 35% of the braid density at the base/proximal end 16. One of ordinary skill in the art will appreciate how to select a braided wire assembly 50 for a particular application of catheter 10.

Braided wire assembly 50 may be formed separately on a disposable core. One or more portions of braided wire assembly 50 may be heat tempered and cooled before incorporation into catheter assembly 26 though methods that are known to those of ordinary skill. The action of heat tempering may help to release the stress on the wire and help reduce radial forces. It is also contemplated that braided wire assembly 50 may be braided directly on catheter assembly 26, for example by passing catheter assembly 26 through a braiding machine during assembly thereof.

FIGS. 2 and 4 respectively depict radial and longitudinal cross-sections of catheter assembly 26 having braided wire assembly 50 encompassed by outer layer 60 before lamination of the materials by heating. In one preferred embodiment, a layer of heat shrink 70 is placed over the top of outer layer 60. Heat shrink 70 is preferably a fluoropolymer or polyolefin material.

Figure 3:
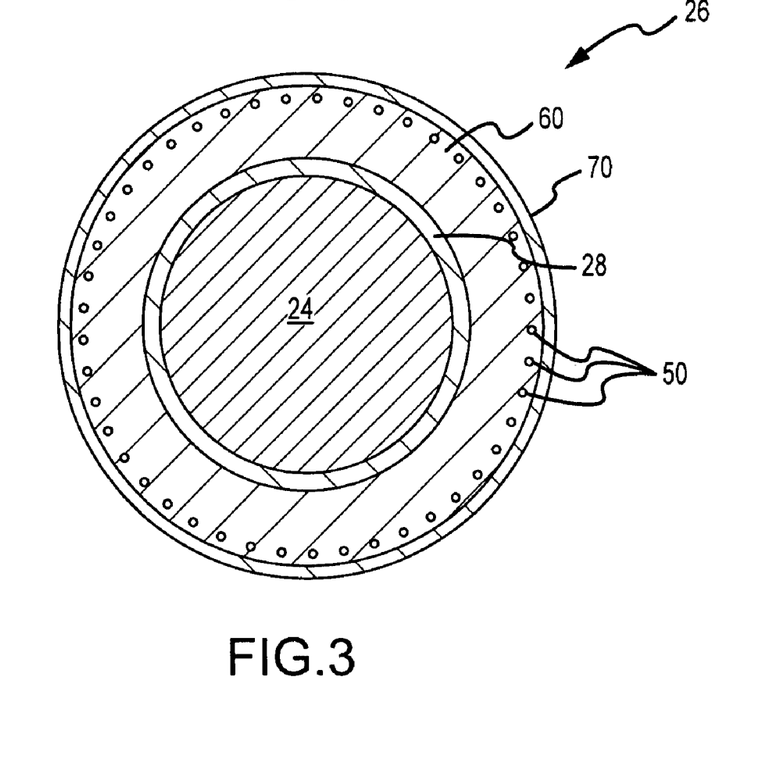
FIG. 3 is a radial cross-sectional view of a catheter body after the application of heat to melt process the outer layer.

FIG. 3 depicts catheter assembly 26 after a lamination process. Catheter assembly 27 may be laminated by heating catheter assembly 26 until the material comprising outer layer 60 flows and redistributes around the circumference thereof as depicted in FIG. 3. Heat shrink 70 has a higher melting temperature than outer layer 60; and during the melt process, heat shrink 70 retains its tubular shape and forces the liquefied outer layer 60 material into braided wire assembly 50 (if present) and into contact with inner liner 28. Catheter assembly 26 may then be cooled. In FIG. 3, both mandrel 24 and heat shrink 70 are still in place.

Figure 5:
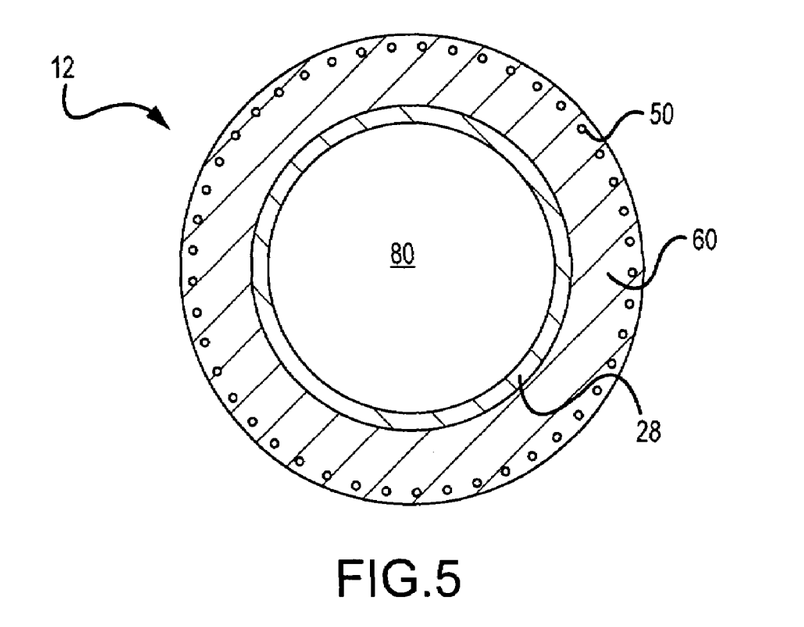
FIG. 5 is a radial cross-sectional view taken along line 5-5 in FIG. 1.

Mandrel 24 may be removed from catheter assembly 26, leaving behind a lumen 80 as illustrated in FIG. 5, which depicts a catheter body made in accordance with the method described above subsequent to the application of heat for the lamination process. Optionally, heat shrink 70 may be left in place around outer layer 60, as depicted in FIG. 3, even after mandrel 24 is removed, such that heat shrink 70 becomes the outermost layer of catheter body 12. If heat shrink 70 is removed, outer layer 60 becomes the outermost layer of catheter body 12. The result is a substantially circular catheter body 12 with a generally circular central lumen 80 and braided wire assembly 50 substantially embedded within outer layer 60 material as illustrated in FIGS. 3 and 5.

Figure 6:
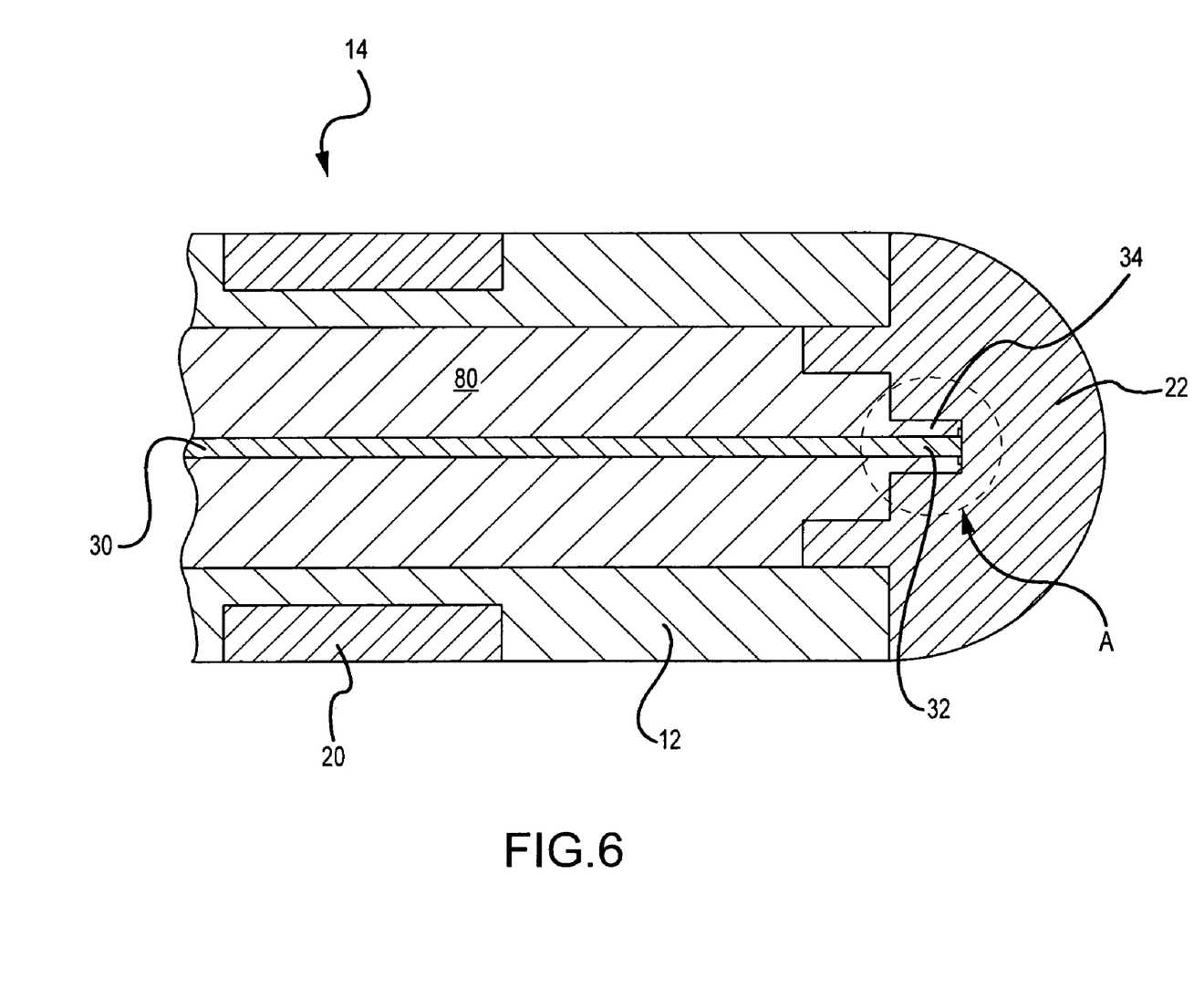
FIG. 6 is a side cut-away view of the distal end of a catheter according to an embodiment of the present invention depicting shape memory alloy wires attached to a tip electrode.

As shown in FIG. 6, which is a side cut-away view of distal end 14 of catheter body 12, a wire 30 may then be placed extending longitudinally through central lumen 80. Wire 30 is attached to catheter body 12 at distal end 14 (e.g., to tip electrode 22) as described below. For the sake of simplicity, catheter body 12 is depicted in FIG. 6 as having only a single layer, though the construction of distal end 14 may be as described above (e.g., including multiple layers, such as inner liner 28 and outer layer 60).

Wire 30 may have any desired cross-section, such as circular, flat, elliptical, or any other shape. For example, a flat wire may be used when it is desirable for catheter 10 to favor deflection along one axis and yet be predisposed to resist deflection along a second, generally orthogonal axis. One preferred embodiment of wire 30 is a wire having an outer diameter of about 0.015" and a substantially circular cross section.

Wire 30 is preferably a shape memory alloy wire, such as a wire containing nickel and titanium (known commercially as NiTi or Nitinol); copper, aluminum, and nickel; or copper, zinc, and aluminum. Wire 30 may function as a steering wire, or pull wire, configured to deflect distal end 14 of catheter body 12 in at least one plane when placed in tension. For a pull wire, the shape memory effect facilitates returning distal end 14 of catheter body 12 to its original, undeflected ("home") position when wire 30 is unloaded (e.g., not placed in tension via a suitable actuator (not shown) on handle 18 of catheter 10). Alternatively, wire 30 may function as a shaping wire that forms distal end 14 of catheter body 12 into a preset geometry, such as a particularly desirable curvature, for example the C-shaped curve described in U.S. application Ser. No. 11/646,578, filed 28 Dec. 2006, which is hereby expressly incorporated by reference as though fully set forth herein. For a shaping wire, the shape memory effect permits catheter body 12 to be deformed, for example for insertion into a patient's body, and then rebound to the preset geometry thereafter, typically when exposed to the increased temperature within the patient's body.

In alternative embodiments, wire 30 may be covered with lubricious materials including silicone, Teflon®, siloxane, and other lubricious materials (not shown), before placement. Alternatively, wire 30 may also be coated with a lubricious layer to promote slideability. It is also contemplated that wire 30 may be manufactured with a smooth surface to promote slideability. While shape memory alloys are preferred for wire 30, other materials are contemplated and regarded as within the spirit and scope of the present invention.

More than one wire 30 may also be used. Each wire may serve as either or both of a shaping wire and a pull wire. That is, in some embodiments of the invention, one or more pull wires may be independent of one or more shaping wires, while, in other embodiments of the invention, one or more wires may serve as both pull wires and shaping wires.

Figure 7:
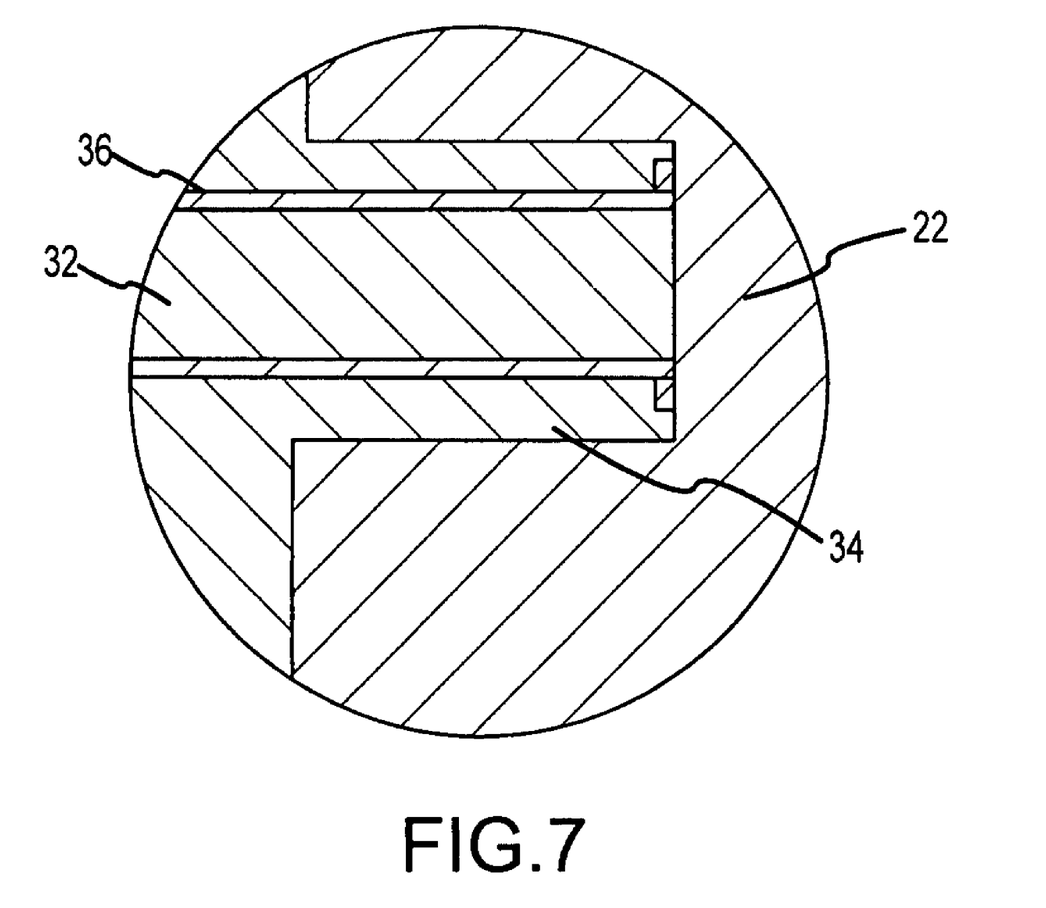
FIG. 7 illustrates the attachment between a shape memory alloy wire and a tip electrode, indicated as region A in FIG. 6.
Figure 8:
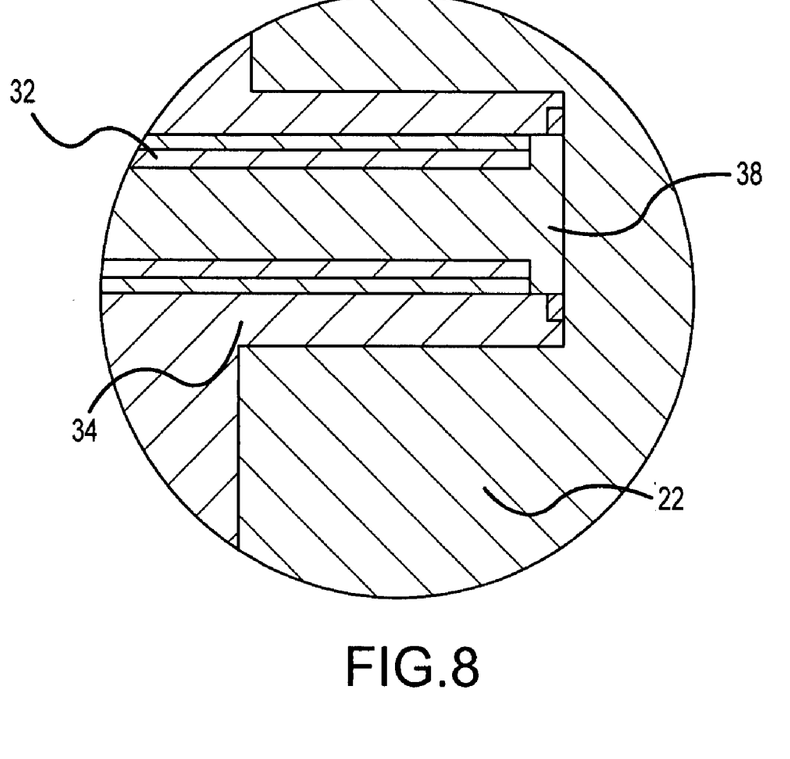
FIG. 8 illustrates an alternative attachment between a shape memory alloy wire and a tip electrode, indicated as region A in FIG. 6.

Wires 30 are joined at their distal ends 32 to tip electrode 22. Preferably, as shown in the details of FIGS. 7 and 8, distal end 32 of wire 30 is fit into a recess 34 in tip electrode 22, where distal end 32 of wire 30 is metallurgically joined to tip electrode 22. As used herein, the term "metallurgically joined" encompasses a number of processes, including, without limitation, soldering, brazing, and welding. In the preferred embodiment of catheter 10, distal end 32 of wire 30 is silver brazed to tip electrode 22.

As shown in the detail of FIG. 7, distal end 32 of wire 30 may be coated with a metal compound 36 that is compatible to be metallurgically joined to tip electrode 22 in order to facilitate metallurgically joining wire 30 to tip electrode 22. Metal compound 36 may be deposited on wire 30 by any suitable method, such as electroplating or sputter-deposition. Further, in addition to coating distal end 32, it is contemplated that any fraction of the length of wire 30, including all or substantially all of the length of wire 30, may be coated with metal compound 36. Suitable metal compounds 36 include, but are not limited to, nickel, copper, brass, and any combinations thereof. Metal compound 36 is preferably selected based, in part, on the metallurgical joining process that is used to join distal end 32 of wire 30 to tip electrode 22, and also based, in part, on the compositions of wire 30 and tip electrode 22.

Preferably, the coating of metal compound 36 adds less than about 0.0005" to the outer diameter of wire 30 (e.g., the coating of metal compound 36 is less than about 0.00025" thick). Advantageously, this permits the use of wires 30 of larger outer diameter, for example where it is desirable to utilize wires 30 to increase the stiffness of catheter body 12, and may also permit the manufacture of catheters 10 of reduced outer diameter (e.g., less than about 5 French, more preferably less than about 4 French, and most preferably of about 3 French).

An alternative method of joining distal end 32 of wire 30 to tip electrode 22 is shown in the detail of FIG. 8. Rather than coating distal end 32 of wire 30 with a metal compound compatible with the selected metallurgical joining process, distal end 32 of wire 30 includes a core 38 of a metal compound compatible with the selected metallurgical joining process, such as nickel, copper, brass, or a combination thereof. It is contemplated that core 38 may extend all or substantially all of the length of wire 30, along any fraction of the length of wire 30, or may be present only near distal end 32 thereof. Core 38 may then be metallurgically joined to tip electrode 22.

Thus, stated more generally, at least distal end 32 of wire 30 preferably includes at least a first material and a second material, with the first material being a shape memory alloy, such as nickel-titanium, copper-aluminum-nickel, or copper-zinc-aluminum, and the second material being a metal compound that is compatible to be metallically joined to tip electrode 22, such as nickel, copper, brass, or a combination thereof. The second material (that is, the compatible metal compound) may form a coating about the first material (that is, the shape memory alloy), as by plating the shape memory alloy with the compatible metal compound. Alternatively, the second material may form a core within the first material. The second material may be metallurgically joined to tip electrode 22, or to another metallic catheter component.

Figure 9:
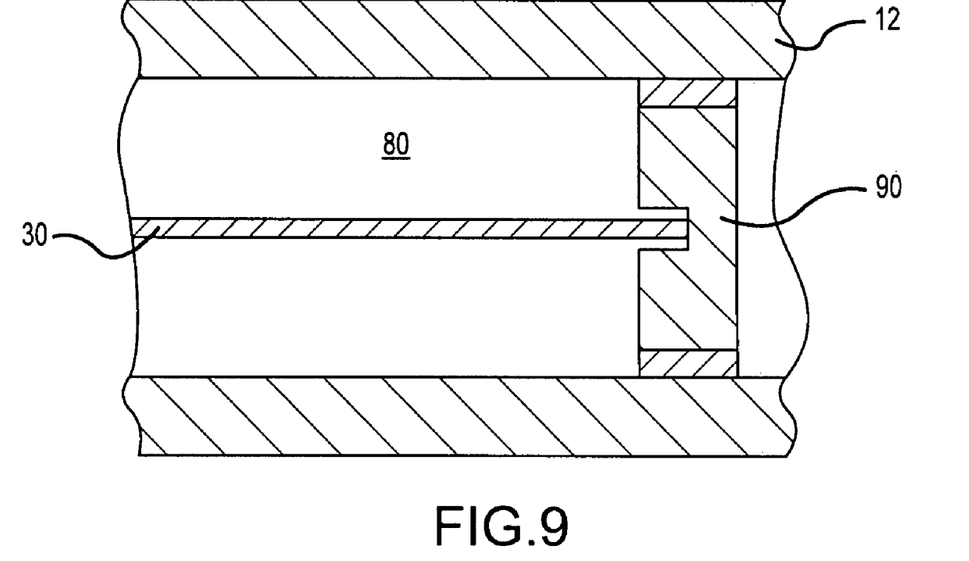
FIG. 9 is a side cut-away view depicting shape memory alloy wires attached to a pull ring.

Although several embodiments of this invention have been described above with a certain degree of particularity, those skilled in the art could make numerous alterations to the disclosed embodiments without departing from the spirit or scope of this invention. For example, it is also contemplated that, rather than being joined to tip electrode 22, wire 30 may instead be joined to one or more other metallic catheter components, such as one or more pull rings 90, as shown in FIG. 9.

Of course, catheter assembly 26 may also be manufactured using alternative techniques. In one embodiment, outer layer 60 may be formed by extruding outer layer 60 over catheter assembly 26. In another embodiment, catheter assembly 26 may formed by using a combination of heat and a press that has a mold for defining the final shape of catheter body 12. It is further contemplated that one or more shape memory alloy shaping or pull wires may be embedded into outer layer 60 during melt processing by placing such wires along inner liner 28 prior to melt processing.

It should also be understood that the diameter of lumen 80 may vary with the intended application of catheter 10; some embodiments of catheter 10 may not include a lumen 80 at all. Alternatively, in other embodiments of the invention, one or more non-central lumens may be provided through which one or more shape memory alloy wires or other catheter components may be routed.

Thus, as one of ordinary skill in the art will readily appreciate, many different configurations and arrangements of the various components and features of catheter assembly 26 are contemplated as within the spirit and scope of the present invention.

Similarly, though the invention has been described in the context of attaching a single shape memory alloy pull wire to the tip electrode in a mono-directional steerable electrophysiology catheter, it is contemplated that the invention could be practiced with equal success in other contexts, including, without limitation, attaching shape memory alloy shaping wires to tip electrodes in spiral electrophysiology catheters. Nor is the invention limited to attaching shape memory alloy shaping and steering wires; the present invention may be employed in any setting in which it is desirable to metallurgically join a shape memory alloy component of any type to a metallic component.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter, comprising:
    an elongate catheter body having a proximal end and a distal end;
    at least one metallic catheter component located at the distal end of the elongate catheter body, the at least one metallic catheter component including a recess; and
    at least one shape memory alloy wire extending at least partially along the elongate catheter body and having a proximal end and a distal end,
    wherein at least the distal end of the at least one shape memory alloy wire is plated with a plating metal that is compatible to be metallurgically joined to the at least one metallic catheter component, and
    wherein the distal end of the at least one shape memory alloy wire is joined to the at least one metallic catheter component within the recess thereof.

2. The catheter according to claim 1, wherein the plating metal comprises nickel.

3. The catheter according to claim 1, wherein the plating metal comprises copper.

4. The catheter according to claim 1, wherein the plating metal comprises brass.

5. The catheter according to claim 1, wherein the plating metal increases an outer diameter of the at least one shape memory alloy wire by no more than about 0.0005".

6. The catheter according to claim 1, wherein the plating metal increases an outer dimension of the at least one shape memory alloy wire by no more than about 0.0010".

7. The catheter according to claim 1, wherein the at least one shape memory alloy wire comprises at least one nickel-titanium wire.

8. The catheter according to claim 1, wherein the at least one shape memory alloy wire comprises at least one copper-aluminum-nickel wire.

9. The catheter according to claim 1, wherein the at least one shape memory alloy wire comprises at least one copper-zinc-aluminum wire.

10. The catheter according to claim 1, wherein the at least one shape memory alloy wire is brazed to the at least one metallic catheter component.

11. The catheter according to claim 10, wherein the at least one shape memory alloy wire is silver brazed to the at least one metallic catheter component.

12. The catheter according to claim 1, wherein the at least one shape memory alloy wire is configured as a pull wire that deflects the distal end of the catheter body in at least one plane.

13. The catheter according to claim 1, wherein the at least one shape memory alloy wire is configured as a shaping wire that forms the distal end of the catheter body into a preset shape.

14. The catheter according to claim 1, wherein the distal end of the catheter body has an outer diameter of about 5 French and the at least one shape memory alloy wire has an outer diameter of about 0.15".

15. The catheter according to claim 1, wherein the distal end of the catheter body has an outer diameter of less than about 4 French.

16. The catheter according to claim 15, wherein the distal end of the catheter body has an outer diameter of less than about 3 French.

17. The catheter according to claim 1, wherein the at least one metallic catheter component comprises at least one electrode.

18. The catheter according to claim 1, wherein the at least one metallic catheter component comprises at least one pull ring.

19. An electrophysiology catheter, comprising:
    a catheter body having a distal end and a proximal end;
    a tip electrode attached to the distal end of the catheter body; and
    at least one shape memory alloy wire extending through the catheter body,
    wherein a distal end of the at least one shape memory alloy wire is plated with a metal compound and the plated end of the at least one shape memory alloy wire is metallurgically joined to the tip electrode.

20. The electrophysiology catheter according to claim 19, wherein the metal compound is selected from the group consisting of: nickel, copper, brass, and any combination thereof.

21. The electrophysiology catheter according to claim 19, wherein the shape memory alloy wire comprises a material selected from the group consisting of: nickel-titanium, copper-aluminum-nickel, and copper-zinc-aluminum.

22. The electrophysiology catheter according to claim 19, wherein the plated end of the at least one shape memory alloy wire is brazed to the tip electrode.

23. A method of manufacturing a catheter, comprising:
    forming an elongate catheter body having a proximal end and a distal end;
    attaching at least one metallic catheter component to the distal end of the catheter body;
    forming a recess in the at least one metallic catheter component;
    coating at least a portion of at least one shape memory alloy wire with a metal compound compatible with a metallurgical joining process; and
    metallurgically joining the coated portion of the at least one shape memory alloy wire to the at least one metallic catheter component within the recess of the at least one metallic catheter component.

24. The method according to claim 23, wherein the step of coating at least a portion of at least one shape memory alloy wire with a metal compound compatible with a metallurgical joining process comprises plating at least a portion of the at least one shape memory alloy wire with a metal compound compatible with a metallurgical joining process.

25. The method according to claim 23, wherein the metal compound comprises nickel.

26. The method according to claim 23, wherein the metal compound comprises copper.

27. The method according to claim 23, wherein the metal compound comprises brass.

28. The method according to claim 23, wherein the step of metallurgically joining the coated portion of the at least one shape memory alloy wire to the at least one metallic catheter component through a metallurgical joining process comprises brazing the coated portion of the at least one shape memory alloy wire to the at least one metallic catheter component.

29. The method according to claim 28, wherein the step of brazing the coated portion of the at least one shape memory alloy wire to the at least one metallic catheter component comprises silver brazing the coated portion of the at least one shape memory alloy wire to the at least one metallic catheter component.

30. The method according to claim 23, wherein the shape memory alloy wire comprises nickel-titanium.

31. The method according to claim 23, wherein the shape memory alloy wire comprises copper-aluminum-nickel.

32. The method according to claim 23, wherein the shape memory alloy wire comprises copper-zinc-aluminum.

33. An electrophysiology catheter, comprising:
an elongate catheter body having a distal end and a proximal end;
a catheter tip that comprises at least one metallic catheter component, said catheter tip being positioned on the distal end of the elongate body, and wherein the at least one metallic catheter component is at least one of a metal null ring and a metal tip electrode; and
at least one internal catheter component joined to the at least one metallic catheter component,
wherein the at least one internal catheter component comprises a first material and a second material, the first material being a shape memory alloy and the second material being a metal compound that is capable of bonding with the first material, and wherein the second material is metallurgically joined to the at least one metallic catheter component.

34. The electrophysiology catheter according to claim 33, wherein the second material comprises a coating about the first material.

35. The electrophysiology catheter according to claim 34, wherein the second material is plated upon the first material.

36. The electrophysiology catheter according to claim 33, wherein the second material comprises a core within the first material.

37. The electrophysiology catheter according to claim 33, wherein the at least one catheter component is configured as a shaping wire that forms the distal end of the catheter body into a preset shape.

38. The electrophysiology catheter according to claim 33, wherein the at least one catheter component is configured as a pull wire that deflects the distal end of the catheter body in at least one plane.

39. A method of manufacturing an electrophysiology catheter, the method comprising:
forming a catheter body having a proximal end and a distal end;
attaching a tip electrode to the distal end of the catheter body;
providing at least one catheter component comprising a first material and a second material, wherein the first material is a shape memory alloy and the second material is a metal compound that is capable of bonding with the first material and being metallurgically joined to the tip electrode; and
metallurgically joining the at least one catheter component to the tip electrode.

40. The method according to claim 39, wherein the step of providing at least one catheter component comprising a first material and a second material comprises plating the shape memory alloy with the metal compound that is compatible to be metallically joined to the tip electrode.

* * * * *